United States Patent [19]

Lee

[11] Patent Number: 4,875,897
[45] Date of Patent: Oct. 24, 1989

[54] CATHETER ASSEMBLY

[75] Inventor: Garrett Lee, Sacramento County, Calif.

[73] Assignee: Regents of University of California, Berkeley, Calif.

[21] Appl. No.: 180,728

[22] Filed: Apr. 6, 1988

Related U.S. Application Data

[63] Continuation of Ser. No. 63,699, Jun. 12, 1981, abandoned, which is a continuation of Ser. No. 913,639, Sep. 30, 1986, abandoned, which is a continuation of Ser. No. 778,278, Sep. 18, 1985, abandoned, which is a continuation of Ser. No. 326,221, Dec. 1, 1981, abandoned.

[51] Int. Cl.$^4$ .............................................. A61M 25/00
[52] U.S. Cl. ...................................... 604/283; 604/28; 604/164; 128/303.1
[58] Field of Search ............ 604/283, 164, 165, 20–22, 604/27, 28, 35–38, 43, 53, 96, 101; 128/303.1, DIG. 9

[56] References Cited

U.S. PATENT DOCUMENTS

| | | | |
|---|---|---|---|
| 3,470,876 | 10/1969 | Barchilon | 128/348 |
| 3,858,577 | 1/1975 | Bass et al. | 128/8 |
| 3,866,599 | 2/1975 | Johnson | 128/248 X |
| 3,900,022 | 8/1975 | Widran | 128/7 |
| 4,040,413 | 8/1977 | Ohshiro | 604/21 X |
| 4,146,019 | 3/1979 | Bass et al. | 128/6 |
| 4,175,545 | 11/1979 | Termanini | 128/348 |
| 4,207,874 | 6/1980 | Choy | 128/6 |
| 4,222,375 | 9/1980 | Martinez | 128/348 X |
| 4,224,929 | 9/1980 | Furihata | 128/6 X |
| 4,269,485 | 5/1981 | Yamashita et al. | 128/4 X |
| 4,273,109 | 6/1981 | Enderby | 128/303.1 X |
| 4,277,168 | 7/1981 | Oku | 128/4 X |
| 4,279,252 | 7/1981 | Martin | 128/349 R |
| 4,290,421 | 9/1981 | Siegmund | 128/6 |
| 4,295,464 | 10/1981 | Shihata | 128/349 BX |
| 4,299,226 | 11/1981 | Banka | 128/349 BX |
| 4,313,431 | 2/1982 | Frank | 128/7 |
| 4,327,720 | 5/1982 | Bronson et al. | 128/349 BX |
| 4,418,688 | 12/1983 | Loeb | 128/6 |

Primary Examiner—John D. Yasko
Attorney, Agent, or Firm—Flehr, Hohbach, Test, Albritton & Herbert

[57] ABSTRACT

A catheter assembly including a first catheter having distal and proximal ends, and a second catheter which is positionable within the first catheter. The second catheter has a smaller diameter and is more flexible than the first catheter. The second catheter is positionable within the first catheter so that its distal end is extendable beyond the distal end of the first catheter. An expandable balloon or inflatable means is affixed to the outer surface of either the first or second catheters near the distal end thereof. When inflated, the inflatable means sealingly engages the interior walls of a body channel into which the catheter assembly has been inserted. The catheter assembly may also include associated fiber optics for viewing and removing obstructions.

31 Claims, 4 Drawing Sheets

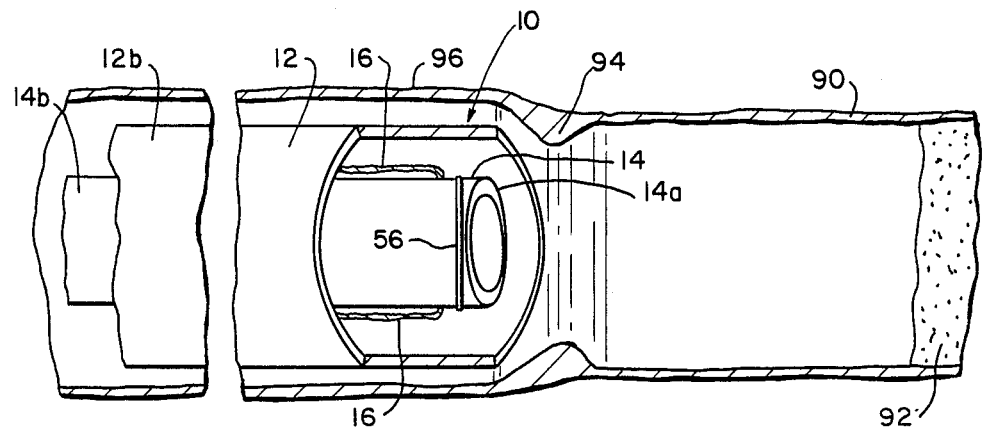
FIG.—1A
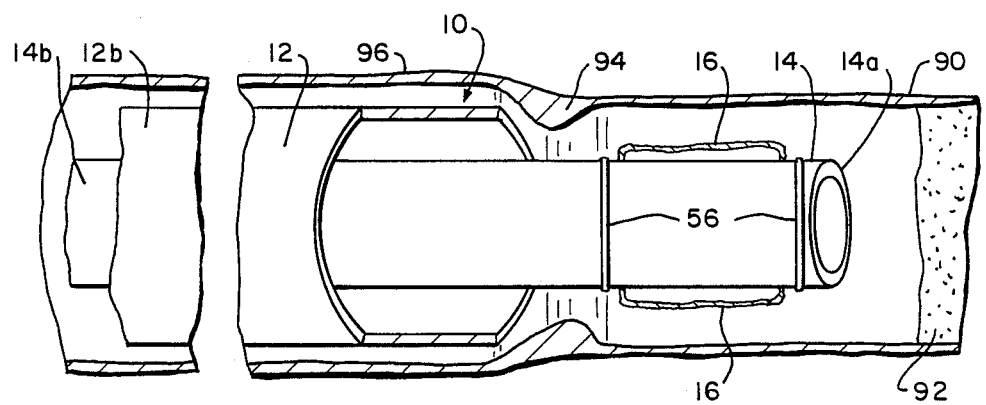
FIG.—1B
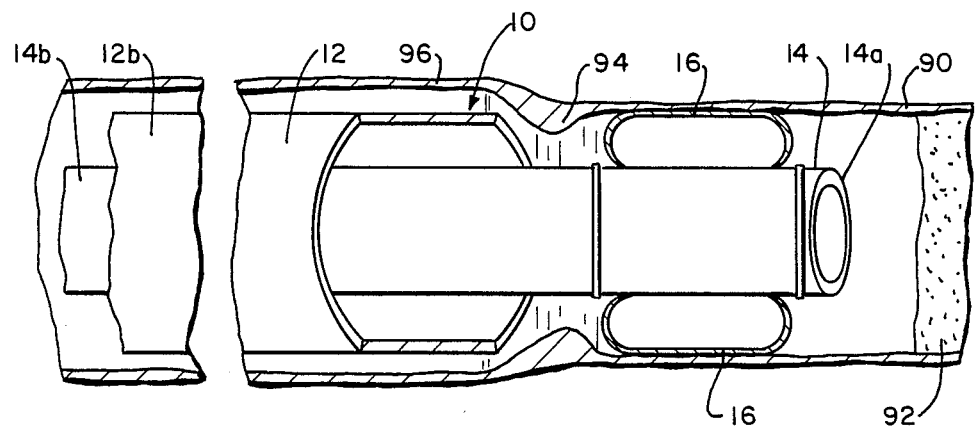
FIG.—1C

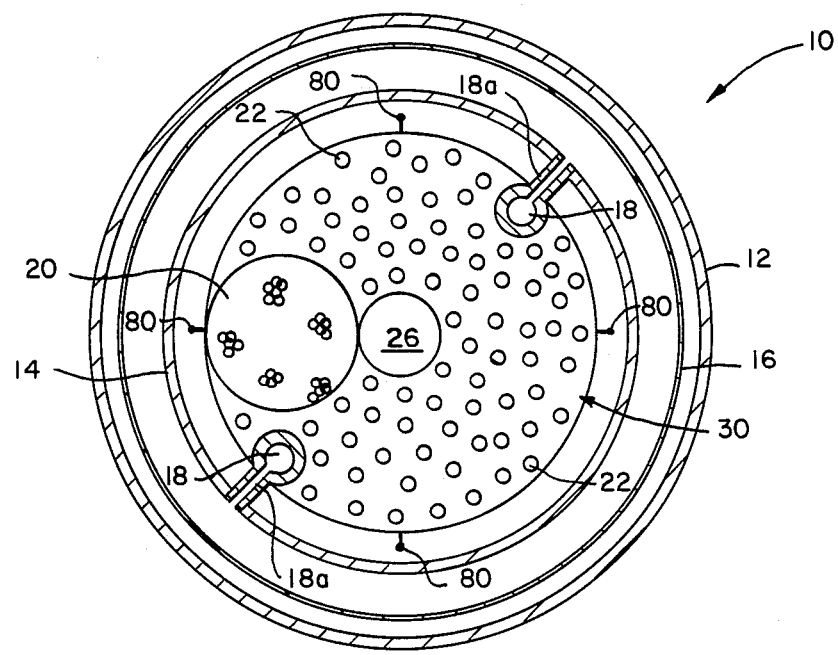
FIG.—2
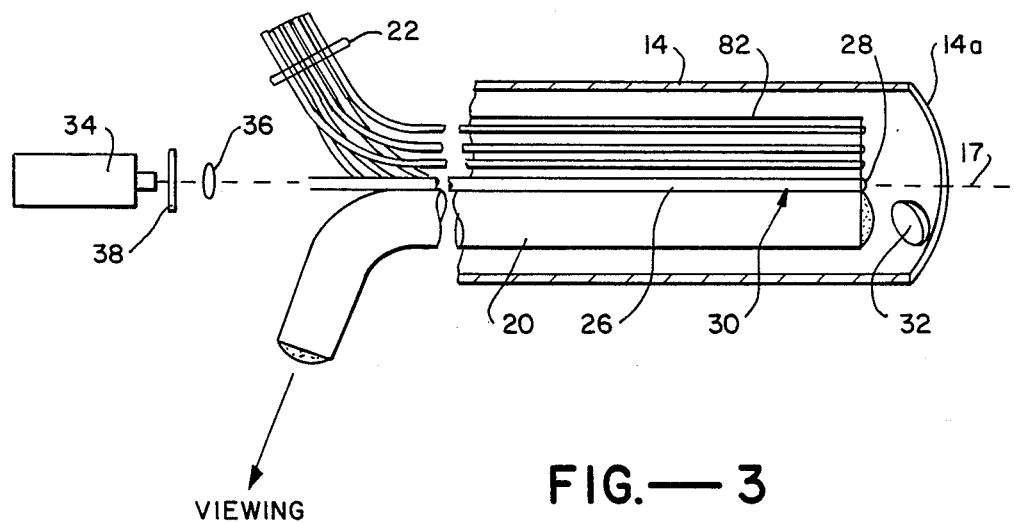
FIG.—3

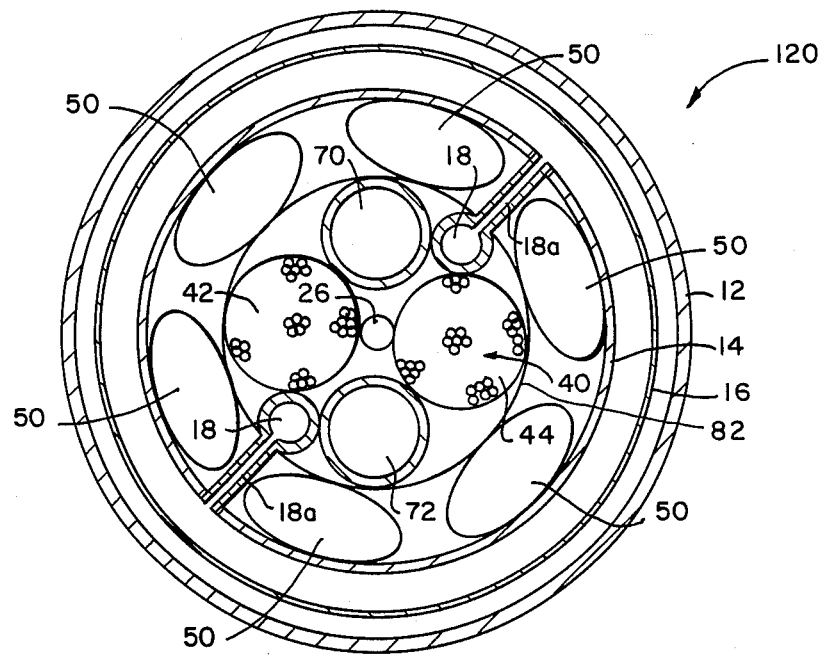
FIG.—4
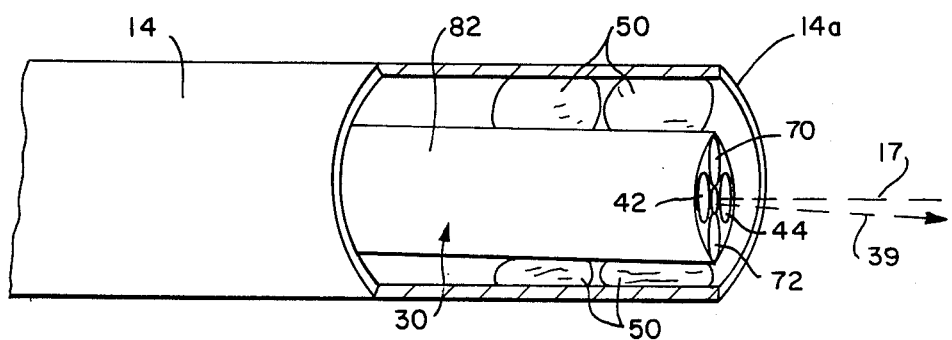
FIG.—5
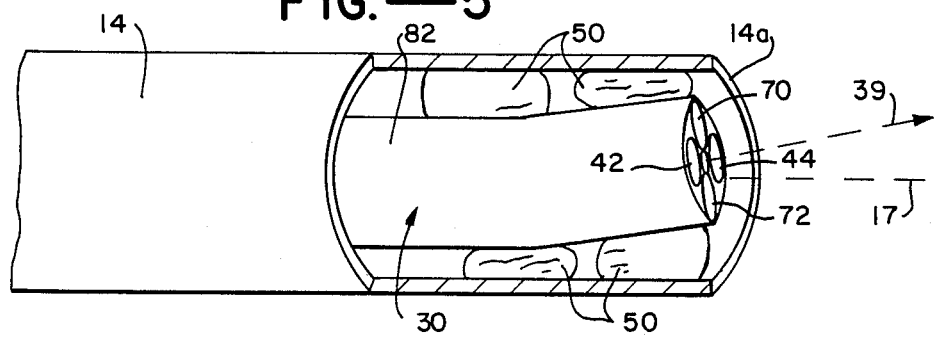
FIG.—6

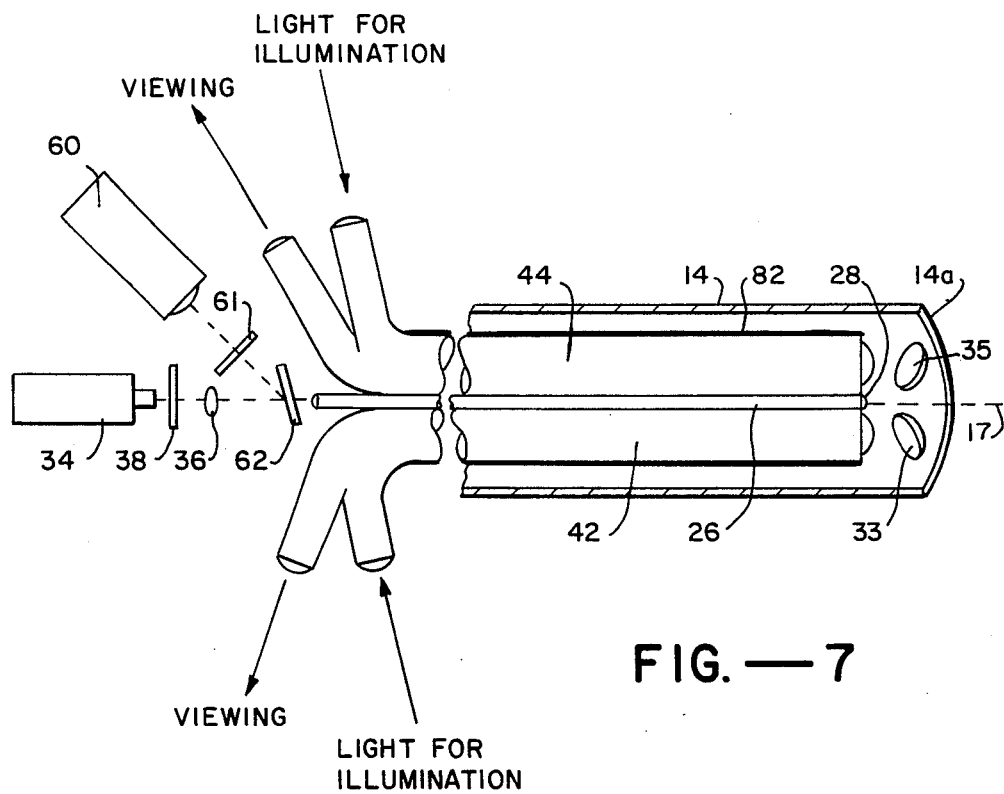
FIG.—7
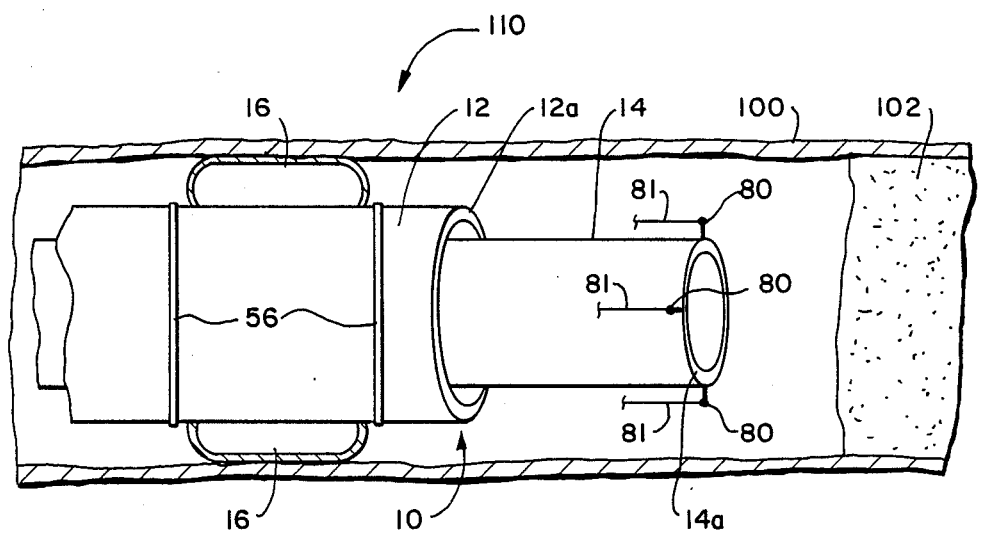
FIG.—8

CATHETER ASSEMBLY

This application is a continuation of Ser. No. 063,699, filed June 12, 1987, which is a continuation of Ser. No. 913,639, filed Sept. 30, 1986, which is a continuation of Ser. No. 778,278, filed Sept. 18, 1985, which is a continuation of Ser. No. 326,721, filed Dec. 1, 1981, all now abandoned.

The present invention relates generally to catheter assemblies, and more particularly to a catheter assembly for diagnostic use or for use in removing an obstruction in a blood vessel, body channel or body cavity.

The American Heart Association has estimated that approximately four million people in the United States suffer from arteriosclerotic coronary artery disease. Many of these people are likely to suffer or die from a myocardial infraction, commonly known as a heart attack. Heart attacks are in fact the leading cause of death in the United States. Thrombosis in the coronary artery beyond the arteriosclerotic constriction is the usual cause of heart attacks. A procedure which can open arteriosclerotic constrictions, thereby permitting the normal flow of blood to the heart, may reduce the many deaths and disabilities caused by heart disease.

Constrictions in the coronary artery are caused by a build-up of plaque, which may be "hard" or "soft". Plaque consists of calcium, fibrous and fatty substances. If the plaque is of recent origin or "soft", that is, it has a low concentration of calcium, a "Grüntzig" balloon catheter may be used to clear the artery. The "Grüntzig" catheter is inserted into the constricted area of the artery, and the balloon is inflated to expand and compress the plaque, thereby opening the artery and permitting an increased flow of blood through the artery. The "Grüntzig" balloon catheter is described in the following article: "Nonoperative Dilatation of Coronary-Artery Stenosis", A.R. Grüntzig, M.D., A. Senning, M.D., and W.E. Siegenthaler, M.D., *The New England Journal of Medicine*, Vol. 301, No. 2, July 12, 1979. See also U.S. Pat. No. 4,195,637, Grüntzig, et al., issued Apr. 1, 1980.

The "Grüntzig" technique, however, does not work where the constriction in the artery is very tight, where the plaque is "old" and hard, or where the plaque forming the constriction has a high concentration of calcium and thus is very hard. It is estimated that the "Grüntzig" technique can be successfully used on only about 5% of the patients suffering from arteriosclerotic coronary disease.

Accordingly, the present invention is directed to a catheter assembly which can remove (a) plaque, especially when hard, and (b) operate in a very constricted area of an artery. The catheter assembly of the present invention may also be used to remove obstructions from other blood vessels and body channels or cavities, as well as to view a region of a blood vessel or a non-vascular body channel.

The present invention also provides a catheter assembly which is able to temporarily interrupt the flow of blood to an occluded or constricted region while such region is treated or observed.

The catheter assembly of the present invention includes a first or outer catheter having distal and proximal ends, and a second or inner catheter which is positionable within the first catheter. The second catheter has a smaller diameter than the first catheter, and preferably, the second catheter is more flexible. The second catheter is positioned within the first catheter so that the second catheter can be shifted or moved with respect to the first catheter. Also, the distal end of the second catheter is extendable past the distal end of the first catheter. Inflatable means such as an expandable balloon is affixed to the outer surface of at least one of the catheters near the distal end thereof. When inflated, the balloon sealingly engages the interior walls of the blood vessel or the like in which the catheter assembly is inserted. This is done to stop the flow of blood into the area of the blood vessel in front of the distal end of the second catheter and thus to facilitate visualization of the obstructed or constricted region.

A plurality of optical fibers extend through a portion of the second catheter and terminate at a point within the second catheter near its distal end. Usually one bundle of optical fibers is used for illuminating and another bundle of optical fibers is used for viewing the area in front of the distal end of the second catheter.

Where the catheter assembly is to be used to remove an obstruction in a blood vessel, such as plaque material in the coronary artery or a clot, a special fiber capable of transmitting energy in the form of a laser beam extends through a portion of the second catheter and terminates near the distal end thereof. An appropriate lens may be attached to that end of the "laser fiber" located at the distal end of the second catheter. The lens focuses and intensifies the laser beam. In order to remove the obstruction, the laser has to deliver to the target area power sufficient to destroy, vaporize or soften the obstruction.

Additionally, one or more channels may be provided within the catheter assembly for removal of combustion material generated during laser irradiation and for flushing of body fluids trapped between an occlusion and the adjacent catheter assembly. Suitable flushing fluids for this purpose are saline solutions, Ringer's solution, and the like. These channels may also be used to infuse a radio-opaque dye in the region.

Appropriate positioning means may also be provided within the catheter assembly for positioning the laser fiber, and the viewing and illuminating optical fibers relative to the central axis of the catheter assembly.

The catheter assembly embodying the present invention may include fiber optics for viewing and illuminating a body region, a fiber optic for transmitting a laser beam to a region within the patient's body, or both types of fiber optics, as desired. Alternatively, both types of fiber optics may be omitted and the catheter assembly of the present invention used to pretreat the plaque, occlusion or clot with a chemotherapeutic substance. In this later embodiment, the catheter assembly could be guided to the occlusion or clot by such means as fluoroscopy. Fluoroscopy could also be used to guide the catheter assembly to the target area where the assembly includes only a laser fiber optic.

The catheter assembly of the present invention will be described in more detail hereinafter in conjunction with the drawings wherein:

FIG. 1A through 1C are schematic, side views, partly in section, illustrating the positioning of the inner catheter within the outer catheter of the catheter assembly of the present invention.

FIG. 2 is a schematic, sectional view of the catheter assembly of the present invention.

FIG. 3 is a schematic, sectional view along the central axis of the inner catheter of the catheter assembly of the present invention.

FIG. 4 is a schematic, sectional view of an alternative embodiment of the catheter assembly of the present invention.

FIGS. 5 and 6 are schematic views, partly in section, of a positioning means used with the catheter assembly of the present invention.

FIG. 7 is a schematic, sectional view along the central axis of the inner catheter illustrating an alternative embodiment of the catheter assembly of the present invention.

FIG. 8 is a schematic, side view of the catheter assembly of the present invention wherein the inflatable means is affixed to the outer surface of the outer catheter.

The present invention will be described in conjunction with its most suitable use: the removal of plaque material from the coronary artery. The catheter assembly of the present invention, however, can also be used to remove occlusions, such as clots, in other arteries and veins. The present invention is especially useful in very constricted areas of blood vessels and for removing very hard material. Further, the catheter assembly could be used where it is necessary to temporarily stop the flow of blood to permit visual inspection and to achieve successful removal of an occlusion. The catheter assembly could also be used without its associated laser apparatus where it is simply desired to view an area of a blood vessel, some non-vascular body channel, or the interior of an organ or cavity. The present invention could also be used to remove obstructions from non-vascular body channels; for example, it could be used to remove bladder, kidney and gall stones.

Referring now to the drawings, in which like components are designated by like reference numerals throughout the various figures, attention is first directed to FIGS. 1A through 1C. FIGS. 1A through 1C show catheter assembly 10 of the present invention positioned for use in removing plaque 92 from coronary artery 90. Catheter assembly 10 comprises a guide or outer catheter 12 and a second or inner catheter 14. Guide catheter 12 has been inserted into an arm, leg or other artery 96 to extend near orifice 94 of the coronary artery. The guide catheter is guided through such artery to the orifice by procedures well known in the art, such as fluoroscopy. Alternatively, catheter 12 may be an existing pre-formed catheter or articulated endoscope, adapted as described herein.

Catheter 14 is positioned in coronary artery 90 by inserting it through guide catheter 12. Catheter 12 guides catheter 14 from the point of insertion, which is at the proximal end 12b of catheter 12, into coronary artery 90. To facilitate movement of catheter 14 within guide catheter 12, catheter 14 is more flexible than catheter 12. Catheter 14 also has a smaller outside diameter than the guide catheter. The outside diameter of catheter 12 is about 2.5 to 3.5 millimeters for use within the coronary artery. For other blood vessels or body channels, the outside diameter of catheter 12 may be selected accordingly. The outside diameter of catheter 14 is approximately 1.5 to 2.5 millimeters. In instances, where the catheter assembly does not include optical fibers for viewing and illuminating, the outside diameter of catheter 14 can be as small as about 1 to 2 millimeters.

In use, catheter 14 is inserted in and pushed through the guide catheter until its distal end 14a extends beyond distal end 12a of the guide catheter, see FIGS. 1A through 1C. Inflatable means 16, discussed in more detail below, is affixed to inner catheter 14 at the distal end thereof. The inflatable means is collapsed as the inner catheter moves through the guide catheter, see FIGS. 1A and 1B. After distal end 14a of the inner catheter has been positioned near plaque buildup 92 by such means as fluoroscopy and the viewing and illuminating fiber optics, which are discussed below, inflatable means 16 is inflated as shown in FIG. 1C. Radio-opaque bands 56 may be located at distal end 14a so that the position of distal end 14a and inflatable means 16 can be precisely determined by use of the fluoroscope.

To illuminate stenotic obstruction 92, an optical fiber bundle comprising a plurality of optical fibers 22 is provided within catheter 14, see FIGS. 2 and 3. Optical fibers 22 originate at an exterior intense viewing light source, which is not illustrated, and extend from the proximal end 14b of catheter 14 to a point within the catheter near its distal end 14a. Optical fibers 22 are used to illuminate the area in front of the distal end of catheter 14.

Catheter 14 further includes an optical fiber bundle 20 consisting of a plurality of optical fibers for viewing the area in front of distal end 14a. Bundle 20 is connected to an appropriate eyepiece, which is not illustrated, and extends from the proximal end 14b of catheter 14 to terminate at a point within the catheter near distal end 14a. If desired, a protective transparent shield may be provided over the distal end of bundle 20. Viewing bundle 20 forms an image that is produced and viewed by conventional means as in a medical endoscope. Bundle 20, which is offset from central axis 17 of catheter 14, collects light through a tilted lens 32. Lens 32 permits observation of the central portion of the artery, the surrounding area, and the occlusion.

A laser-beam transmitting fiber 26 for transmission of laser energy from a laser source 34 is also carried by catheter 14. Laser-transmitting fiber 26 extends from proximal end 14b of catheter 14 to a point inwardly of but near the distal end of catheter 14. Fiber 26 is preferably located along the central axis of catheter 14, and may also be covered by a transparent shield if desired.

Laser 34 is coupled to laser-transmitting fiber 26 by a lens 36, which is either placed between the laser and the laser-transmitting fiber, as illustrated, or which is incorporated into the optical fiber. The exterior surface of laser transmitting fiber 26 is coated with an anti-reflective coating for the laser wavelength of interest. A shutter 38 between laser 34 and lens 36 permits control of laser irradiation. Endoscopes used in conjunction with lasers for the performance of surgery are discussed in U.S. Pat. No. 3,858,577, issued Jan. 7, 1975, Bass, et al., and U.S. Pat. No. 4,146,019, issued Mar.27, 1979, Bass, et al. The disclosures in these two patents are hereby incorporated by reference.

Laser 34 has to deliver to the target area sufficient power at the predetermined wavelength to destroy, vaporize or soften plaque material 92. The laser beam should be conducted through optical fiber 26 with as little power loss as feasible. Additionally, the laser should interact with the plaque material rather than with the surrounding normal tissue of the artery or any infrared liquid that may be present. Several types of lasers can be used, for example, argon-ion, carbon dioxide, and Neodynium YAG lasers. Lasers having a wavelength capable of destroying or softening plaque but without adverse effect on blood cells or tissue are preferred. For lasers of certain wavelengths, for instance, carbon dioxide lasers, some laser-transmitting guide other than an optical fiber might have to be used.

To achieve the high intensities required for destruction of plaque material 92, the laser is focused by a short-focal length lens 28. Lens 28 is either spaced from the end of optical fiber 26, or, as shown, affixed to the end of optical fiber 26. Lens 28 may comprise a plurality of lenses.

The laser will destroy blood cells present and may produce blood clotting in the area of the targeted occlusion. Clotting in the occluded coronary artery would further compromise blood flow to the heart. Thus, laser surgery in the coronary artery requires that blood flow to the targeted occlusion be stopped. Catheter assembly 10 includes an inflatable or expandable balloon 16 for temporarily stopping the flow of blood into the area in front of the distal end of catheter 14. Blood flow in the coronary artery, however, cannot be interrupted for more than 12 to 15 seconds without endangering the patient's life. By temporarily interrupting the flow of blood, blood can be excluded from the region, the obstructed or constricted area can be viewed, and the obstruction can be successfully removed. The region in front of the distal end of catheter 14 can also be flushed with a solution, such as Ringer's or saline, to dilute any blood present in that region. Perhaps, a gas such as carbon dioxide could also be injected into this region to expand the artery, and to clear blood from the ends of the optical fibers.

Inflatable balloon 16 is circumferentially affixed about the exterior surface of catheter 14, and is located near the distal end of catheter 14. Prior to opening shutter 38, balloon 16 is inflated to sealingly engage the interior walls of coronary artery 90, thereby stopping the flow of blood into the area of targeted occlusion 92, see FIG. 1C. The laser will vaporize the occlusion within a time period of less than one second depending upon the type and power of laser used. Afterwards, balloon 16 may be deflated to permit blood flow through the coronary artery, or if time permits, catheter 14 may be extended further to remove or soften an additional section of plaque before the flow of blood is restored.

As balloon 16 only has to stop the flow of blood and not expand the artery, the balloon can be inflated by lower pressures and be constructed of less rigid materials than a "Grüntzig"-type balloon. Alternatively, balloon 16 may be constructed to stop blood flow as well as to expand soft plaque or any other deformable construction in an artery.

In an alternate embodiment, as illustrated in FIG. 8, catheter assembly 10 may have inflatable means 16 circumferentially affixed about the exterior surface of catheter 12 near the distal end 12a thereof. This embodiment is particularly useful in the removal of plaque or clot 102 found in a peripheral vessel 100, such as the iliar and femoral arteries.

A pair of channels 18, see FIG. 2, extend through catheter 14 and are connected to the interior of balloon 16 by means of a flexible tubing 18a. A gas, such as carbon dioxide, or a liquid, such as saline, is passed through channels 18 from a source, which is not illustrated, to expand balloon 16. To deflate the balloon, the gas or fluid may be withdrawn from the balloon by means of these channels. Channels 18 may also be built into the wall of catheter 14.

A cable pulley arrangement is provided to position catheter 14 which carries the laser, illumination, and viewing fiber optics. As shown in FIG. 2, the cables are attached at appropriate points 80 to a sheath 82 which is disposed circumferentially about optical fibers 22, viewing bundle 20, and laser fiber 26. Sheath 82 may extend the length of the optical fibers back to proximal end 14b of catheter 14. Sheath 82 defines a grouping 30 of fiber optics within the central section of catheter 14. The grouping includes viewing bundle 20, laser optical fiber 26, and illumination optical fibers 22. As in gastroendoscopy, the cable pulley arrangement can be operated to tilt grouping 30 or to cause it to move transversely relative to the central axis of the catheter assembly. This permits viewing and laser irradiation of sites in the artery which are not centrally located with respect to catheter 14. Alternatively, as shown in FIG. 8, cables 81 of the cable pulley arrangement may be attached at appropriate points 80 to the outside surface of catheter 14 at the distal end thereof. The illumination fiber optics of catheter 10 have been described as comprising a plurality of individual optical fibers 22 disposed within catheter 14. It is to be understood, however, that a fiber optical bundle, like bundle 20, could be fashioned to include both illumination and viewing optical fibers. Such an approach is described below.

An alternative embodiment of the catheter assembly of the present invention is illustrated in FIGS. 4 through 7. In that embodiment, catheter assembly 120 includes two fiber optical bundles 42 and 44 to provide binocular vision, and thus depth perception of the target area. Each bundle 42 and 44 in turn includes an illumination bundle portion connected to an intense light source for illuminating the area in front of distal end 14a, and a viewing bundle portion connected to an eyepiece for viewing the area in front of distal end 14a.

Bundles 42 and 44 are located on either side of the central axis of catheter 14, and they collect light through their own respective tilted lenses 33 and 35. The lenses are suitably tilted to allow observation of the central portion of the artery as well as the surrounding area. This stereoscopic binocular approach permits perception of depth within the artery. As in the embodiment described above, bundles 42 and 44 permit observation of a wide area of the coronary artery, as well as the .obstruction and laser focal spot.

The embodiment illustrated in FIG. 7 also includes an intense coherent light source 60 which is located between laser 34 and laser fiber optic 26. Light source 60 is slightly offset from the laser propagation axis. Light source 60 permits viewing of the precise region of the laser focus as well as the exact size of the focused laser beam. An optical filter 61 and a beam splitter 62 are located between light source 60 and laser fiber optic 26 to help distinguish the laser focal region from the region of general illumination. Light source 60 serves as an aiming beam or target light when lasers having an invisible wavelength are used.

Catheter assembly 120 further includes a flushing tube 70 and a suction tube 72. Both of these tubes extend within catheter 14 from its proximal end 14b to a point inwardly of distal end 14a, see FIGS. 4 through 6.

Flushing tube 70 is provided for injecting a flushing fluid, such as saline or Ringer's solution, into the area between the distal end of catheter 14 and the occlusion. The flushing fluid can be injected to dilute and/or remove any trapped blood, after blood flow to the occlusion is stopped by balloon 16. A radio-opaque dye may also be injected into this area through flushing tube 70 so that the dye may be viewed on a fluoroscope to determine the site of the obstruction. A gas such as carbon dioxide could also be injected through flushing tube 70. Suction tube 72, which is connected to an appropriate filtering system outside of catheter 14, is designed to remove the aforesaid diluted blood and flushing fluid, dye, or any products that may form after the plaque material has been vapored or otherwise removed by the laser.

Grouping 30 of catheter assembly 120 includes laser-transmitting fiber optic 26, and fiber optic bundles 42 and 44. Grouping 30 also includes flushing and suction tubes 70 and 72. To position grouping 30, a series of positioning balloons 50 are disposed circumferentially about the grouping. Inflatable balloons 50 are each operably connected to independent pressure sources, which are not illustrated, via tubes, also not illustrated, extending from the proximal end of catheter 14. As with the cable pulley arrangement, inflatable balloons 50 permit grouping 30 to move transversely and tilt relative to the central axis of the catheter assembly. The positioning-balloon system permits viewing and laser irradiation of sites that are not centrally located relative to the central axis of catheter 14.

As shown in FIGS. 5 and 6, where reference numeral 39 represents the central axis of grouping 30, by inflating some balloons and deflating others, grouping 30 can be appropriately positioned relative to the target area. FIG. 5 shows an arrangement where grouping 30 has been moved transversely with respect to the central axis of the catheter assembly. FIG. 6 shows an arrangement in which grouping 30 has been moved transversely and tilted.

In other embodiments, the catheter assembly of the present invention could employ more than one laser.

The laser-transmitting fiber could also be offset from the central axis of the inner catheter and could use a tilted or nonsymmetrical lens. Different configurations of the viewing and illuminating optical fibers are also possible.

Although certain specific embodiments of the invention have been described herein in detail, the invention is not to be limited to only such embodiments, but rather only by the appendant claims.

What is claimed is:

1. A catheter assembly, comprising:
    an outer catheter for insertion into a body channel, said outer catheter having distal and proximal ends;
    an inner catheter positionable within said outer catheter and having a distal end that is extendable toward the distal end of said outer catheter;
    an inflatable means affixed to the outer surface of at least one of said catheters for forming a seal at the interior walls of the body channel;
    optical fibers extending through a portion of said inner catheter for illuminating and viewing the area in front of the distal end of said inner catheter; and
    means for positioning said optical fibers relative to the axis of said outer catheter.

2. The catheter assembly of claim 1 wherein said positioning means includes a cable and pulley arrangement.

3. The catheter assembly of claim 1 wherein said optical fibers for illuminating and viewing include:
    a plurality of optical fibers extending through a portion of said inner catheter and terminating within said inner catheter near the distal end thereof for use in illuminating the area in front of the distal end of said inner catheter; and
    a fiber optic bundle extending through a portion of said inner catheter and terminating within said inner catheter near the distal end thereof for use in viewing the area in front of the distal end of said inner catheter.

4. The catheter assembly of claim 1 further including a flushing channel extending through a portion of said inner catheter and terminating within said inner catheter near the distal end thereof.

5. The catheter assembly of claim 1 further including an optical fiber extending through a portion of said inner catheter for transmitting laser energy therethrough for removing an obstruction outwardly of the distal end of said inner catheter.

6. The catheter assembly of claim 5 further including means for positioning said laser optical fiber relative to the central axis of said outer catheter.

7. The catheter assembly of claim 6 wherein said positioning means includes a cable arrangement.

8. The catheter assembly of claim 5 further including:
    flushing and suction channels extending through a portion of said inner catheter and terminating within said inner catheter near the distal end thereof.

9. The catheter assembly of claim 5 wherein said viewing and illuminating optical fibers include:
    a plurality of optical fibers extending through a portion of said inner catheter and terminating within said inner catheter near the distal end thereof for use in illuminating the area in front of the distal end of said inner catheter; and
    a fiber optic bundle extending through a portion of said inner catheter and terminating within said inner catheter near the distal end thereof for use in viewing the area in front of the distal end of said inner catheter.

10. The catheter assembly of claim 5 wherein said viewing and illuminating optical fibers comprise:
    a fiber optical bundle having a viewing bundle portion for viewing the area in front of the distal end of said inner catheter, and a light source bundle portion for illuminating said area.

11. The catheter assembly of claim 10 wherein there are two of said fiber optical bundles disposed on opposite sides of the central axis of said inner catheter.

12. A catheter assembly for use in removing an obstruction in a blood vessel, comprising:
    a first catheter for insertion into the blood vessel, sand first catheter having distal and proximal ends;
    a second catheter having distal and proximal ends and of smaller diameter than said first catheter, said second catheter positionable within said first catheter such that the distal end of said second catheter is extendable toward the distal end of said first catheter;
    inflatable means affixed at the exterior surface of at least one of said catheters near the distal end thereof for sealing against interior walls of the blood vessel when inflated to prevent the flow of blood into the area of the obstruction;
    optical fibers extending through said second catheter and terminating near the distal end thereof for use in illuminating and viewing the obstruction;
    at least one optical fiber extending through said second catheter and terminating near the distal end of said second catheter for transmitting laser energy therethrough to remove the obstruction; and
    means for positioning said viewing and illuminating optical fibers, and said laser fiber relative to the central axis of the first catheter.

13. The catheter assembly of claim 12 wherein said laser fiber is positioned along the central axis of said second catheter.

14. The catheter assembly of claim 12 wherein that end of said laser fiber terminating near the distal end of said second catheter includes a lens for focusing a laser beam on the obstruction.

15. The catheter assembly of claim 12 wherein said positioning means includes a cable arrangement.

16. The catheter assembly of claim 12 further including:
   a flushing tube extending through a portion of said second catheter and terminating within said second catheter near the distal end thereof for injecting a flushing fluid, a gas, or a dye into the area in front of the distal end of said second catheter; and
   a suction tube extending through a portion of said second catheter and terminating within said second catheter near the distal end thereof for removing said injected fluid, dye and gas, or materials and gases produced by removal of the obstruction.

17. A method for removing an obstruction in a blood vessel, comprising:
   inserting a first catheter into the blood vessel to a point near the obstruction to act as a guide for a second catheter, said first and second catheters having distal and proximal ends;
   inserting said second catheter into said first catheter so that the distal end of said second catheter extends toward the distal end of said first catheter in proximate relation to the obstruction;
   illuminating and viewing the obstruction by means of optical fibers extending through a portion of said second catheter and terminating near the distal end thereof;
   inflating an expandable member affixed at the outer surface of at least one of said catheters near the distal end thereof to seal against the interior walls of the blood vessel so as to block the flow of blood into the area of the obstruction;
   positioning a laser optical fiber which extends through at least a portion of the second catheter relative to the axis of the second catheter; and
   focusing and transmitting a laser beam through the laser optical fiber to remove the obstruction.

18. The method of claim 17 further including injecting a fluid into the area of the obstruction through a flushing tube extending through said second catheter.

19. The method of claim 18 further including removing through a suction tube extending through said second catheter said fluids, and materials and gases produced by removal of the obstruction.

20. The catheter assembly of claim 12 wherein said viewing and illuminating optical fibers comprise first and second fiber optic bundles each having a viewing bundle portion for viewing the area in front of the distal end of said second catheter and a light source bundle portion for illuminating said area.

21. A catheter assembly, comprising:
   an outer catheter for insertion into a body channel, said outer catheter having distal and proximal ends;
   an inner catheter positionable within said outer catheter and having a distal end extendable toward the distal end of said outer catheter;
   an inflatable means associated with at least one of said catheters for effecting a seal at the interior walls of the body channel;
   optical fibers extending through at least a portion of said inner catheter for illuminating and viewing the area in front of the distal end of said inner catheter; and
   means for positioning said optical fibers relative to the axis of said outer catheter.

22. A catheter assembly, comprising:
   a first catheter for insertion into a body channel, said first catheter having distal and proximal ends;
   a second catheter of smaller diameter than said first catheter and positionable within said first catheter such that a distal end of said second catheter is extendable toward the distal end of said first catheter;
   inflatable means associated with at least one of said catheters near the distal end thereof for effecting a seal at the interior walls of the body channel to prevent the flow of a body fluid therepast; and
   first and second fiber optical bundles for viewing the area in front of the distal end of said second catheter and a light source bundle for illuminating said area.

23. A catheter assembly for removing an obstruction, comprising:
   an outer catheter insertable into a body channel, said outer catheter having distal and proximal ends;
   an inner catheter having distal and proximal ends and of smaller diameter than said outer catheter and positionable within said outer catheter such that the distal end of said inner catheter is extendable toward the distal end of said outer catheter;
   inflatable means associated with at least one of said catheters for effecting a seal at the interior walls of the body channel to prevent the flow of a body fluid therepast and into the of the obstruction;
   means carried by said inner catheter for illuminating and viewing the obstruction; and
   means for transmitting laser energy through said inner catheter for removing the obstruction.

24. The catheter assembly of claim 23 wherein said illuminating and viewing means comprises optical fibers extending through said second catheter and terminating near the distal end thereof; and
   said laser transmitting means comprises at least one optical fiber extending through said second catheter and terminating near the distal end thereof.

25. The catheter assembly of claim 23 further including means for positioning said viewing and illuminating means and said laser transmitting means relative to the central axis of said outer catheter.

26. A catheter assembly comprising:
   a catheter for insertion into a body channel, the catheter having distal and proximal ends;
   an inflatable means associated with the catheter for forming a seal at the interior walls of a body channel;
   optical fibers extending through at least a portion of the catheter for illuminating and viewing the area in front of the distal end of the catheter; and
   mans for positioning aid optical fibers relative to the axis of the catheter.

27. The catheter assembly of claim 26 wherein said positioning means includes a cable means.

28. The catheter assembly of claim 26 further including a channel extending through at least a portion of said catheter.

29. The catheter assembly of claim 26 further including an optical fiber extending through at least a portion of the catheter for transmitting laser energy therethrough for removing an obstruction outwardly of the distal end of said catheter.

30. The catheter assembly of claim 29 further including means for positioning said laser optical fiber relative to the central axis of the catheter.

31. A method for removing an obstruction in a blood vessel, comprising:
 inserting a first catheter into the blood vessel to a point near the obstruction to act as a guide for a second catheter, said first and second catheters having distal and proximal ends;
 inserting said second catheter into said first catheter so that the distal end of said second catheter extends toward the distal end of said first catheter in proximate relation to the obstruction;
 illuminating and viewing the obstruction by means of optical fibers extending through a portion of said second catheter and terminating near the distal end thereof;
 inflating an expandable member associated with at least one of said catheters to effect a seal at the interior walls of the blood vessel so as to block the flow of blood into the area of the obstruction;
 positioning a laser optical fiber which extends through at least a portion of the second catheter relative to the axis of the first catheter; and
 focusing and transmitting a laser beam through the laser optical fiber to remove the obstruction.

* * * * *

UNITED STATES PATENT AND TRADEMARK OFFICE
CERTIFICATE OF CORRECTION

PATENT NO. : 4,875,897
DATED : October 24, 1989
INVENTOR(S) : Garrett Lee

It is certified that error appears in the above—identified patent and that said Letters Patent is hereby corrected as shown below:

Claim 23, Col. 10, line 35, insert --area-- before "of".

Claim 26, Col. 10, line 60, delete "aid" and insert --said--.

Signed and Sealed this

Seventh Day of August, 1990

Attest:

HARRY F. MANBECK, JR.

*Attesting Officer*     *Commissioner of Patents and Trademarks*